United States Patent [19]
Wang

[11] Patent Number: 6,006,590
[45] Date of Patent: *Dec. 28, 1999

[54] METHOD AND APPARATUS FOR ANALYZING FLOWABLE PRODUCTS

[75] Inventor: Jianjun Wang, Columbus, Ohio

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/904,120

[22] Filed: Jul. 31, 1997

Related U.S. Application Data

[63] Continuation of application No. 08/623,721, Mar. 29, 1996, abandoned.

[51] Int. Cl.[6] .................................................. G01N 29/00
[52] U.S. Cl. ............................................................. 73/64.53
[58] Field of Search .................................... 73/602, 61.75, 73/61.49, 61.45, 61.79, 64.53, 52; 128/660.01, 660.07, 661.08

[56] References Cited

U.S. PATENT DOCUMENTS

| | | | |
|---|---|---|---|
| 3,760,634 | 9/1973 | Birks | 73/67.8 R |
| 4,223,790 | 9/1980 | Yoshida | 209/590 |
| 4,428,235 | 1/1984 | Sugiyama | 73/579 |
| 4,466,442 | 8/1984 | Hilmann et al. | 128/653 |
| 4,763,525 | 8/1988 | Cobb | 73/599 |
| 4,907,453 | 3/1990 | Marlow et al. | 73/584 |
| 4,914,966 | 4/1990 | White, Jr. et al. | 73/863.01 |
| 5,152,180 | 10/1992 | Waldhauer, Jr. | 73/579 |
| 5,271,404 | 12/1993 | Corl et al. | 128/661.08 |
| 5,287,753 | 2/1994 | Routh et al. | 73/861.25 |
| 5,311,781 | 5/1994 | Gates | 73/861.25 |
| 5,333,508 | 8/1994 | Petroff et al. | 73/861.25 |
| 5,421,211 | 6/1995 | Heckman | 73/861.25 |
| 5,443,071 | 8/1995 | Banjanin et al. | 128/661.09 |
| 5,487,387 | 1/1996 | Trahey et al. | 128/660.02 |

FOREIGN PATENT DOCUMENTS

| | | |
|---|---|---|
| 0 139 235 | 5/1985 | European Pat. Off. . |
| 85/00123 | 1/1985 | WIPO . |

*Primary Examiner*—Hezron Williams
*Assistant Examiner*—Richard A. Moller
*Attorney, Agent, or Firm*—Brian R. Woodworth; Daniels J. Hulseberg

[57] ABSTRACT

A method and system for ultrasonically analyzing flowable products. The method includes the steps of providing a flowable product to be ultrasonically analyzed. In addition the method includes the steps of providing a means for generating and receiving ultrasonic waves, a processing unit, and a means for agitating the flowable product. A flowable product is agitated using the means for agitating. The means for generating and receiving ultrasonic waves is then placed in ultrasonic contact with the flowable product and ultrasonic waves are directed into the flowable product. Ultrasonic waves are received using the means for generating and receiving ultrasonic waves and the received waves are transmitted to the processing unit where they are processed by establishing respective vectors for a plurality of reflective contents of the flowable product and by comparing the respective vectors to a predetermined, acceptable statistical range of vectors. The system includes a means for conveying a flowable product where the means for conveying includes an agitating means for agitating the flowable product. The system further includes a means for generating and receiving a plurality of ultrasonic waves, a means for selectively placing the means for generating and receiving in ultrasonic contact with the flowable product on said means for conveying, and a processing means for analyzing ultrasonic waves received by the means for generating and receiving. The processing means includes a means for establishing respective vectors for a plurality of reflective contents of the flowable product and a means for comparing the respective vectors to a predetermined, acceptable statistical range of vectors.

17 Claims, 2 Drawing Sheets

METHOD AND APPARATUS FOR ANALYZING FLOWABLE PRODUCTS

This application is a Continuation of application Ser. No. 08/623,721, filed Mar. 29, 1996 abandoned.

BACKGROUND OF THE INVENTION

The present invention is directed to a method and an apparatus for analyzing a product. More particularly, the present invention is directed to a method and an apparatus for performing ultrasound evaluations of products using noninvasive techniques.

The use of ultrasonic imaging techniques in the analysis of solid and liquid products is well-known. Ultrasonic waves generated by a transducer are directed into the target product and a receiver is used to receive the ultrasonic waves that are reflected by or transmitted through the target product. The wave pattern received by the receiver can then be analyzed for the purpose of discerning a number of different characteristics of the target product. For example, ultrasonic imaging techniques can be used for the purpose of identifying voids or other physical flaws in solid products. In addition, ultrasonic imaging can be used to detect the presence of particulate matter and air bubbles in liquids. However, the analysis of ultrasound images can be subjective, thereby resulting in false positive and false negative analyses. In addition, the analysis of ultrasound images can be time-consuming, thereby significantly increasing the costs associated with this process. For these reasons, it is desirable to have a method and apparatus for performing ultrasound evaluations of products that provide an objective and quick analysis of the contents of the product.

SUMMARY OF THE INVENTION

The present invention provides a method and apparatus for conducting ultrasound analysis of products. The method of the present invention includes the steps of providing a product to be analyzed and providing an ultrasound transducer and receiver for conducting an ultrasonic analysis of the provided product. The ultrasound transducer and receiver are activated such that ultrasound waves are directed into the target product and such that reflected or transmitted waves are received by the receiver. The wave pattern received by the receiver is transmitted to a processing unit. The processing unit analyzes the wave pattern on a pixel basis and assigns a gray value to each pixel based upon the strength of the ultrasound signal received by each pixel. The processing unit compares at least a portion of the resulting digital image to a standard image in order to determine whether the product is acceptable.

In an alternative embodiment of the method of the present invention, a flowable product, an ultrasound transducer, and an ultrasound receiver are provided. The flowable product is agitated in order to impart motion therein. The ultrasound transducer and receiver are activated such that a series of ultrasound waves are directed into the product and such that a series of reflected or transmitted waves are received by the receiver. A plurality of wave patterns received by the receiver are transmitted to a processing unit. The processing unit analyzes at least two of the plurality of the received wave patterns and establishes a plurality of vectors based upon the movement reflective contents of the flowable product. The processing unit then compares the resulting plurality of vectors to a predetermined, acceptable vector parameter in order to determine whether the product is acceptable.

The apparatus of the present invention includes an ultrasonic transducer and receiver which are mounted so that they can be placed in ultrasonic contact with a product. The ultrasonic receiver is connected to a processing unit which is configured to analyze wave patterns received by the receiver and to assign a value to each pixel of the wave pattern based upon the strength of the ultrasound signal received therein. The processing unit is further configured to compare at least a portion of the resulting digital wave image to a standard image in order to determine whether the product is acceptable.

In an alternative embodiment of the apparatus of the present invention, the apparatus includes an ultrasonic transducer and receiver which are mounted so that they can be placed in ultrasonic contact with a flowable product. The apparatus further includes an agitating means for agitating a flowable product that is to be ultrasonically analyzed by the apparatus and a means for selectively placing the ultrasonic transducer and receiver in ultrasonic contact with the flowable product. The ultrasonic receiver is connected to a processing means which is configured to analyze wave patterns received by the receiver. The processing means includes a means for establishing vectors that reflect the movement of reflective contents of the flowable product and a means for comparing the vectors to a predetermined, acceptable window or range of statistical parameters of vectors.

BRIEF DESCRIPTION OF THE DRAWINGS

For a more complete understanding of the present invention, reference may be had to the following Detailed Description read in connection with the accompanying drawings in which.

DETAILED DESCRIPTION

Figure 1:
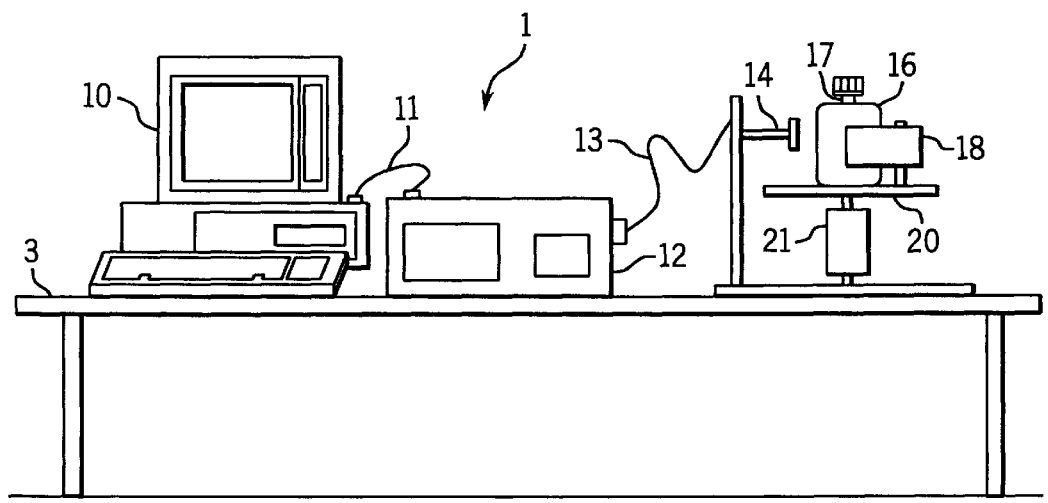
FIG. 1 is a schematic representation of a first embodiment of the apparatus of the present invention.

A system constructed in accordance with the present invention is generally depicted at 1 in FIG. 1. System 1 includes processing unit 10 which preferably controls operation of system 1. As depicted in FIG. 1, processing unit 10 is a computer system controlled by software or hardware, e.g., a computer chip having the requisite programming embedded therein. The function of processing unit 10 will be described in greater detail below.

System 1 further includes ultrasonic transducer 14. In the preferred embodiment of the present invention depicted in FIG. 1, ultrasonic transducer both emits and receives ultrasonic waves. For the purposes of this disclosure, system 1 will be referred to as including a single transducer 14 constructed to emit and receive ultrasonic waves. However, it will be appreciated that separate ultrasonic transducers 14 can be used for emitting and receiving ultrasonic waves without departing from the scope and spirit of the present invention as claimed in the appended claims. In addition, multiple ultrasonic transducers 14 can be used simultaneously in accordance with the present invention. Finally, ultrasonic transducer(s) 14 can be either a single or an array-type transducer of known construction and operation. In the preferred embodiment of the present invention, ultrasonic transducer 14 is configured such that ultrasonic waves emitted therefrom are focused.

Ultrasonic transducer 14 is mounted such that it can be brought into ultrasonic contact with product 16. The term "ultrasonic contact" as used herein refers to a physical relationship wherein ultrasonic waves emitted from ultrasonic transducer 14 are substantially transmitted into product 16. As depicted herein, product 16 is contained in a container 17 constructed of any material known to be permeable to ultrasonic signals, e.g., plastic, glass, metal, and combinations thereof.

Ultrasonic contact can be established between ultrasonic transducer 14 and product 16 by placing an ultrasound coupling gel on an exterior surface of container 17 and placing ultrasonic transducer 14 in contact with the ultrasound coupling gel. Ultrasonic contact also can be established between ultrasonic transducer 14 and product 16 by spraying a liquid, preferably water, on an exterior surface of container 17, or by immersing container 17 in a liquid, preferably water, and then bringing ultrasonic transducer 14 into contact with the liquid surrounding the exterior surface of container 17. In the preferred embodiment of the present invention, ultrasonic contact is created between ultrasonic transducer 14 and product 16 using a gel-less technique. One example of a gel-less technique is described in U.S. Pat. No. 5,494,038 to Wang, et al. which is incorporated herein by reference. In a first embodiment disclosed in U.S. Pat. No. 5,494,038, the gel-less technique employs a membrane that defines pores therethrough. The membrane defines a chamber that contains a liquid acoustical couplant such as water. Ultrasonic transducer 14 can be placed in contact with the membrane defining the chamber. The pores defined through the membrane are sized such that molecules of the liquid acoustical couplant can become entrained therein or pass therethrough, thereby placing the ultrasonic transducer and the surface of the target object in what will be referred to as indirect contact with the liquid acoustical couplant, i.e., in contact through the porous membrane. Through the resulting indirect contact between the transducer and the liquid acoustical couplant and between the liquid acoustical couplant and the surface of the target object, ultrasonic waves emitted by the ultrasonic transducer are directed into a target object.

In a second embodiment disclosed in U.S. Pat. No. 5,494,038, the gel-less technique employs a membrane defining pores therethrough and the wave emitting/receiving end of the ultrasonic transducer to define a chamber. That is, in the second embodiment, the ultrasonic transducer is in direct contact with the liquid acoustical couplant. A liquid acoustical couplant, e.g., water, is disposed in the chamber. The pores of the membrane are sized such that molecules of the liquid acoustical couplant can become entrained therein or pass therethrough, thereby placing the surface of the target object in indirect contact with the liquid acoustical couplant in the chamber. Through the direct contact between the transducer and the liquid acoustical couplant and the indirect contact between the liquid acoustical couplant and the surface of the target object, ultrasonic waves emitted by the ultrasonic transducer are directed into the target object. It will be appreciated that various modifications can be effected to the gel-less techniques disclosed in U.S. Pat. No. 5,494,038.

In the preferred embodiment of the present invention, a transducer control system 12 of known construction and operation is coupled via cable 13 to ultrasonic transducer 14. Transducer control system 12 also is coupled via cable 11 to processing unit 10. Transducer control system 12 controls the operating parameters, e.g., frequency, amplitude, and dynamic focusing, of ultrasonic transducer 14 by directing control signals through cable 13. Ultrasonic waves received by ultrasonic transducer 14 are transferred through cable 13 to transducer control system 12, such transfer occurring directly or occurring after ultrasonic transducer 14 converts the received wave signal to a form interpretable by transducer control system 12. Transducer control system 12 then converts the received ultrasonic wave pattern into a wave image signal that is readable by processing unit 10 and transfers the resulting wave image signal via cable 11 to processing unit 10. It will be appreciated that the functions of processing unit 10, transducer control system 12, and ultrasonic transducer 14 can be combined into a single unit having each of these components' respective functions as discussed herein. Transducer control system 12 preferably can be adjusted by an operator to provide the desired ultrasonic wave parameters and to provide the desired wave image to processing unit 10.

In the embodiment of the present invention depicted in FIG. 1, system 1 is configured to be mounted on table 3. In this embodiment, a platform 20 is provided to support product 16 thereon. Platform 20 can be configured for rotation. In those embodiments of the present invention in which platform 20 can be rotated, such rotation can be effected manually or by the selective operation of a rotational drive system 21 of known construction. Container retainer 18 is mounted on platform 20 and is configured to releasably retain container 17 on platform 20 in order to prevent movement of container 17 relative to platform 20. Ultrasonic transducer 14 and platform 20 are constructed such that ultrasonic transducer 14 can be placed in ultrasonic contact with product 16 in container 17. In the embodiment of the present invention depicted in FIG. 1, platform 20 is slidable such that it can be moved to place ultrasonic transducer 14 in ultrasonic contact with product 16. In this embodiment, drive system 21 is preferably configured to impart linear movement and rotational movement to platform 20. In an alternative embodiment, ultrasonic transducer 14 is mounted such that it can be moved linearly toward and into contact ultrasonic contact with product 16 in container 17.

Figure 2:
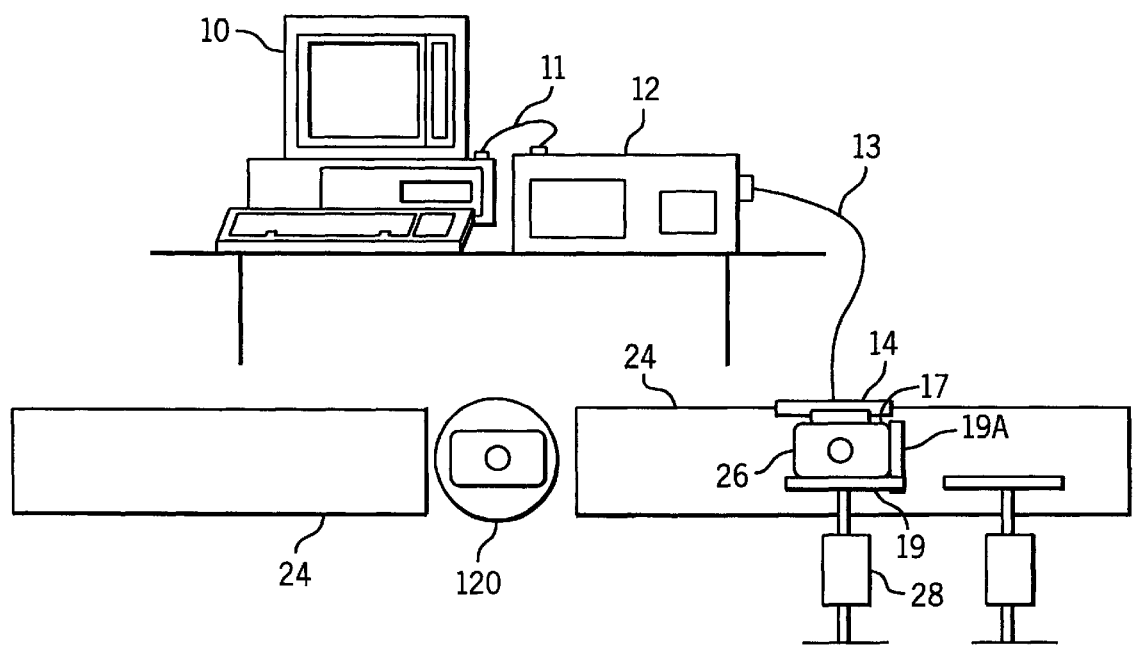
FIG. 2 is a schematic representation of a second embodiment of the apparatus of the present invention.

In the embodiment of the present invention depicted in FIG. 2, system 1 is configured to be part of a system in which a plurality of products 16 in containers 17 are conveyed along a predetermined path, for example, an assembly line. In this embodiment, conveyor 24 is provided to move containers 17 towards ultrasonic transducer 14. Conveyor 24 can be any of a variety known means for conveying products, including, but not limited to, conveyor belts and star wheels. In the embodiment depicted in FIG. 2, conveyor 24 includes agitator 120 which imparts a rotational movement to container 17 and product 16. The importance of imparting movement to product 16 will be discussed in detail below. Agitator 120 also can be configured to impart other types of agitation to container 17 and product 16. For example, agitator 120 can be configured to impart vibratory energy to container 17 in order to effect random movement of product 16 within container 17. Alternatively, agitator 120 can be configured to impart motion to product 16 in any desired plane.

In the embodiment of the present invention depicted in FIG. 2, conveyor 24 carries container 17 to analysis position 26. When container 17 is in analysis position 26, product 16 in container 17 can be placed into ultrasonic contact with ultrasonic transducer 14. Ultrasonic contact between ultrasonic transducer 14 and product 16 in container 17 can be effected by moving ultrasonic transducer 14 into contact with container 17 or by moving container 17 into contact with ultrasonic transducer 14 as above-discussed with respect to the embodiment of the present invention depicted in FIG. 1. In the preferred embodiment of the present invention depicted in FIG. 2, container 17 is moved by piston mechanism 28 such that container 17 is placed in ultrasonic contact with ultrasonic transducer 14. In the embodiment of the present invention depicted in FIG. 2, plate 19 and retainer 19A are mounted on piston mechanism 28 and are configured to restrain container 17 therebetween.

It will be appreciated that other configurations of the embodiment depicted in FIG. 2, are possible. For example, ultrasonic transducer 14 can be mounted on a rotatable head such that ultrasonic transducer 14 is brought into ultrasonic contact with container 17 and as container 17 is moved past analysis position 26. In addition, ultrasonic transducer 14 can be mounted on a piston mechanism whereby it can be moved into and out of ultrasonic contact with products 16 in containers 17 carried by conveyor 24.

Rejection piston mechanism 30 is provided and is constructed to remove designated containers 17 from conveyor 24, as discussed in detail below.

Figure 3:
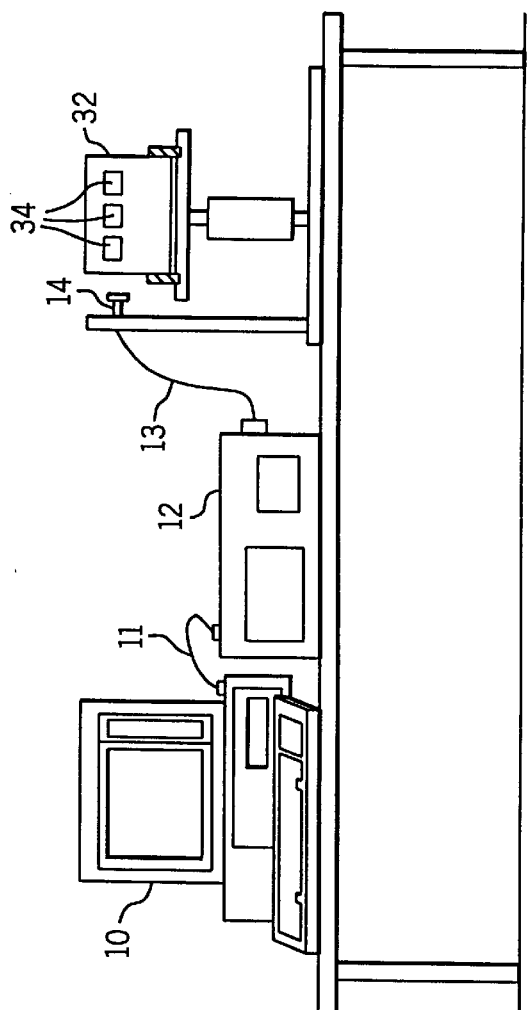
FIG. 3 is a schematic representation of a third embodiment of the apparatus of the present invention.

FIG. 3 depicts an alternative embodiment of the present invention configured for the concurrent or serial analysis of a plurality of products 16 in a plurality of containers 17. As depicted in FIG. 3, processing unit 10 is coupled via cable 11 to ultrasonic controller 12 which in turn is coupled via cable 13 to ultrasonic transducer 14. Ultrasonic transducer 14 can be a single transducer/receiver, or ultrasonic transducer 14 can include multiple transducers/receivers configured for the simultaneous or sequential ultrasonic analysis of a plurality of products 16 contained in collective package 32. Ultrasonic transducer 14 as depicted in FIG. 3 is positioned on one side of collective package 32. In an alternative configuration of the embodiment of the present invention depicted in FIG. 3, two or more ultrasonic transducers 14 are positioned in various locations about the periphery of collective package 32, thus facilitating the ultrasonic analysis of each unit of product 16 contained in collective package 32.

Collective package 32 can be any of a variety of known packaging types. For example, collective package 32 can be a paper, cardboard, plastic, or metal box/retaining device defining apertures 34 therethrough. Collective package 32 also can be a plastic shrink-wrap material or a paper, cardboard, plastic, or metal multi-unit retaining device, e.g., a conventional six-pack retainer. Apertures 34 are configured to provide an access port to each container 17 contained in collective package 32, thereby enabling the ultrasonic analysis of each unit of product 16 in containers 17. Apertures 34 can provide direct access between an external environment and containers 17 in collective package 32, or apertures 34 can be covered in whole or in part by an ultrasonically conductive material. In the embodiment depicted in FIG. 3, collective package 32 is designed to contain six (6) units of product 16 in two rows of three units each. However, it will be appreciated that collective package 32 can be designed to contain any number of containers 17 in any number of configurations, provided that each container 17 in collective package 32 can be placed in ultrasonic contact with at least one ultrasonic transducer 14 associated with system 1. In those embodiments of collective package 32 in which containers 17 are arranged in more than one row, collective package 32 and/or ultrasonic transducer 14 will need to be rotated about the periphery of collective package 32 in order to enable ultrasonic transducer 14 to be placed in ultrasonic contact with product 16 in each container 17. In the alternative, a plurality of ultrasonic transducers 14 can be placed on opposite sides of collective package 32, thereby enabling product 16 in containers 17 in both rows of collective package 32 to be ultrasonically analyzed without the need to rotate either ultrasonic transducer 14 or collective package 32.

System 1 is configured for the ultrasonic testing of one or more units of product 16. System 1 provides a capacity for the static or dynamic ultrasonic analysis of product 16. Static testing can be used to provide a variety of information regarding solid products, flowable products, or products that have both solid and flowable components. Dynamic testing can be used to provide a variety of information regarding flowable products or products that have both solid and flowable components. Dynamic testing can be used with solid products solely for the purpose of confirming that the product is solid or identifying empty containers.

In a static testing procedure, product 16 is not agitated. Thus, when system 1 is operated in a static testing mode, platform 20 does not rotate or otherwise agitate product 16. When system 1 is operated in a dynamic testing mode, platform 20 agitates product 16. As above-discussed, in the preferred embodiment of the present invention, platform 20 agitates product 16 by rotating container 17 about an axis. It will be appreciated that platform 20 in the preferred embodiment of the invention can be configured to rotate any number of degrees, provided that the rotation is sufficient to impart movement to product 16 in container 17. In addition, the speed profile, i.e., speed and acceleration, at which platform 20 agitates product 16 in container 17 can be varied dependent upon the nature of the product 16 and the operating parameters of processing unit 10, ultrasonic control system 12, and ultrasonic transducer 14.

Static testing can be used to provide a variety of information regarding product 16 in container 17, including the detection of air bubbles, foreign substances, or structural flaws in product 16. Static testing can be used to analyze product 16 for the purposes of determining whether container 17 has been underfilled or overfilled. Static testing also can be used to analyze the overall consistency of product 16.

Dynamic testing can be employed to provide all of the information provided with static testing. In addition, dynamic testing can be used to analyze the flow characteristics of product 16 following agitation thereof. Due to changes that occur to some products 16 when they are tainted or spoiled, the flow of product 16 can be used to identify spoiled or tainted product. For example, milk products tend to become more viscous when they are spoiled. Accordingly, it is possible to determine whether a milk product is spoiled by analyzing the flow rate of the milk product using a dynamic testing technique in accordance with the present invention.

In a static testing procedure conducted in accordance with the present invention, product 16 is placed in ultrasonic contact with ultrasonic transducer 14. As depicted in FIGS. 1–3, product 16 can be contained by container 17 which in turn is retained on platform 20 by container retainer 18. It is to be appreciated that static testing can be conducted in a tabletop configuration of system 1 as depicted in FIGS. 1 and 3, or in a conveyor configuration of system 1 as depicted in FIG. 2. As above-indicated, ultrasonic contact between product 16 and ultrasonic transducer 14 can be established by placing a liquid couplant on an exterior surface of container 17 or by immersing container 17 in a liquid couplant. However, in the preferred embodiment of the present invention, a gel-less technique is employed to establish the requisite ultrasonic contact between ultrasonic transducer 14 and product 16.

The characteristics of product 16 can be determined using static testing by directing ultrasonic waves from ultrasonic transducer 14 into product 16. In those embodiments of the present invention in which ultrasonic transducer 14 is configured to emit and receive ultrasonic waves, ultrasonic transducer 14 will receive a wave pattern from product 16 which has been altered as a result of reflections and deflections of the emitted ultrasonic wave caused by the components of product 16. It is well-known in the art that the various components of an object, e.g., air bubbles and particulates, will cause reflections/defections of an ultrasonic wave, thereby enabling the creation an ultrasonic image of the object. As above-discussed with respect to the apparatus of the present invention, ultrasonic transducer 14, in combination with ultrasonic controller 12, processes the received ultrasonic wave and transforms it into a form that is readable by processing unit 10. The transformed wave image is transmitted from ultrasonic controller 12 to processing unit 10 through cable 11. It is to be appreciated that cable 11 and/or cable 13 can be omitted in the event that radio communication is available between ultrasonic transducer 14 and ultrasonic controller 12 and/or between ultrasonic controller 12 and processing unit 10. Further, cables 11 and/or 13 can be omitted when ultrasonic transducer 14 and ultrasonic controller 12 are combined and/or when ultrasonic controller and processing unit 10 are combined.

Processing unit 10 analyzes the transformed wave image on a pixelby-pixel basis and assigns a numerical gray scale value to each pixel. As used herein, the term "pixel" refers to a finite region within the wave image. The pixels can have a variety of geometric configurations and dimensions, although in common practice the pixels typically will be rectangular or square. The number of pixels used will be determined by the capacity of processing unit 10 and the characteristics of product 16 undergoing analysis. In one embodiment of the present invention, processing unit 10 analyzes the transformed wave image using 22,000 pixels arranged in a 220×100 configuration. One of ordinary skill in the art will appreciate that other pixel arrangements are possible without departing from the spirit and scope of the present invention.

The magnitude of the gray scale value assigned to each pixel is determined by the intensity of the signal in each pixel. A mean gray scale value for the wave image can be calculated by summing each assigned gray scale value and dividing the sum by the number of pixels. The mean gray scale value for the wave image will be higher than an acceptable mean gray scale value where the number of particulates, coagulations, foreign objects, and/or air bubbles in product 16 is higher than acceptable. Thus, an acceptable range of mean gray scale values for product 16 can be established by analyzing units of product 16 that have been previously deemed acceptable using known testing techniques, e.g., microbiological, physical, chemical, and visual testing, and combinations thereof. Processing unit 10 can then compare the calculated mean gray scale value to the acceptable range of mean gray scale values for product 16 in order to determine whether the unit of product 16 undergoing analysis is acceptable. In the event that the calculated mean gray scale value is not within the acceptable range, processing unit 10 preferably generates an error signal indicating that the unit of product should be discarded. In the embodiment of the invention depicted in FIG. 2, rejection piston mechanism 30 is controlled by processing unit 10 and is activated upon generation of an error signal. Upon activation of rejection piston mechanism 30, the unacceptable unit of product 16 will be pushed from conveyor 24 into a discarded position. It will be appreciated that other known mechanisms for removing an unacceptable unit of product 16 can be employed without departing from the scope of the present invention. For example, unacceptable units of product 16 can be discarded manually.

Static testing also can be used for the purpose of identifying foreign objects in product 16. Upon the assignment of gray scale values for each pixel of the wave image, processing unit 10 will analyze the assigned values for the purpose of identifying large gray scale value deviations from one pixel to the next. Unlike air bubbles and coagulations, foreign objects will tend to produce higher intensity images and therefore will have a higher gray scale value. Thus, the occurrence of a significant variation in gray scale value from pixel-to-pixel will tend to indicate the presence of a foreign object in product 16. In this static testing mode, processing unit will compare the variations of gray scale values of the wave image to an acceptable range of variations to determine whether product 16 contains an unacceptable foreign object. Here again, the acceptable range of variations of gray scale values can be determined by testing units of product 16 that have been proven to be acceptable using other techniques. It will be appreciated that the gray scale deviation standard employed by processing unit 10 to identify the presence of a foreign object in product 16 will vary dependent upon the nature of product 16. In the event that processing unit 10 detects an unacceptable foreign object in product 16, processing unit 10 will generate an error signal as above-discussed.

Static testing also can be used to indicate the fill level of product 16 within container 17. Due to the nearly infinite resistance of air to ultrasonic waves, there will be a discontinuation in the wave image at the interface between product 16 and air within container 17. Processing unit 10 can identify this interface by analyzing the gray scale values of the wave image for the purpose of establishing the air/product interface. Upon identifying the location of the interface, processing unit 10 compares the fill level of container 17 to an acceptable range of fill levels to determine whether container 17 is overfilled or underfilled. In the event that the interface location does not fall within a preselected acceptable range of fill levels, processing unit 10 will generate an error signal as above-discussed. It will be appreciated that the positioning of ultrasonic transducer 14 relative to container 17 must be controlled in order to provide accurate fill information. System 1 of the present invention is configured to provide a fixed relationship between ultrasonic transducer 14 and product 16 when product 16 is undergoing analysis.

Dynamic testing differs from static testing in that two or more wave images received by processing unit 10 are analyzed in order to determine certain characteristics of product 16. As above-discussed, each of the analyses that can be performed using static testing can be conducted by analyzing a single image of a dynamic test, that is, any one of a plurality of images. However, rather than analyzing a static product, these tests analyze a snapshot of a dynamic product, i.e., a product in motion. Product 16 is set in motion by an agitator. As above-discussed with respect to the apparatus of the present invention, a variety of known types of agitators can be used to impart different types of motion to product 16 in container 17. For the purposes of this disclosure, the motion imparted by the agitator will be a rotational motion created by the rotation of platform 20. However, it will be appreciated that the dynamic testing techniques described herein apply to all motions that can be imparted to product 16.

In a dynamic testing procedure conducted in accordance with the method of the present invention, a flowable product 16 is set in motion within container 17 by the rotation of platform 20. Ultrasonic transducer 14 is then brought into ultrasonic contact with product 16 as above-discussed. Ultrasonic transducer 14 emits a plurality of ultrasonic waves which enter product 16 and are then received by ultrasonic transducer 14. Ultrasonic transducer 14 and ultrasonic controller 12 transform the received wave images into a form that is readable by processing unit 10 and the transformed wave images are transmitted to processing unit 10 for analysis.

In accordance with the present invention, processing unit 10 assigns gray scale values on a pixel-by-pixel basis to a first of the plurality of wave images received by processing unit 10 from ultrasonic transducer 14 and ultrasonic controller 12, thereby establishing a reference for further analysis of product 16. In accordance with the preferred embodiment of the present invention, processing unit 10 analyzes the gray scale values assigned to each pixel for the purpose of identifying those pixels that have a threshold value. Pixels having a gray scale value higher than the predetermined threshold value reflect the presence of air bubbles, particulates, foreign objects, or coagulants in product 16. For the purposes of this disclosure, air bubbles, particulates, foreign objects, and coagulants will be referred to as "reflective contents" of product 16. These reflective contents can be identified in the wave image by reflective images 52 as depicted in FIG. 4. Although FIG. 4 depicts only a single reflective image 52, it will be appreciated that a plurality of reflective images 52 will be present in the wave image undergoing analysis by processing unit 10. The threshold value used by processing unit 10 to identify reflective contents will vary dependent upon the product undergoing analysis and the purpose of the test. The threshold value preferably is preprogrammed into processing unit 10.

In analyzing the assigned gray scale values, processing unit 10 analyzes a neighborhood 50 around each pixel having a gray scale value at least as great as the threshold value for the purpose of identifying the periphery of each reflective content represented by a reflective image 52. Processing unit 10 establishes the periphery of each reflective image 52 by identifying pixels in neighborhood 50 that do not have a gray scale value at least as large as the threshold value. Processing unit 10 then calculates the center or mass center 56 of each of the reflective images 52 based upon the identified periphery thereof. In the preferred embodiment, processing unit 10 calculates the mass center of each of the reflective images 52 based upon the identified periphery thereof and the individual pixel gray scale values. Use of mass center in this analysis is advantageous in that it enables processing unit 10 to better identify individual reflective contents moving through product 16. In one embodiment of the present invention, processing unit 10 is configured such that it will generate an error signal in the event that the dimensions of the reflective image 52 are larger than a predetermined threshold value, thereby indicating the presence of a foreign object or an undesired coagulation of agglomeration. It will be appreciated that this portion of the dynamic analysis of product 16 can also be conducted on a static basis.

Processing unit 10 subsequently conducts the same analyses of a second of the plurality of received wave images for the purpose of identifying the center or mass center of each of the reflective images 52 of the reflective contents of product 16 in the subsequent image. It is preferred that the second wave image analyzed by processing unit 10 reflect a "snapshot" of product 16 at a time sufficiently subsequent to the time of the first wave image such that the reflective contents of product 16 have been given adequate time to move. The desired time delay between the first and second analyzed wave images will vary based upon the degree of agitation imparted to product 16 and based upon the viscosity of product 16. If a high degree of agitation is imparted to product 16, or if product 16 has a relatively low viscosity, it is preferable that the first and second analyzed wave images be relatively close in time. If a relatively low degree of agitation is imparted to product 16, or if product 16 has a relatively high viscosity, it is preferable that the first and second analyzed wave images be farther apart in time.

Vectors 54 can be established to represent the movement of the centers or mass centers 56 of each reflective image 52 from the first analyzed wave image to the second analyzed wave image. By assigning x and y axis values to each position of each reflective image 52 in each analyzed wave image, the displacement of the center or mass center 56 of each reflective image 52, and thus the magnitude of each vector 54, can be established using the Pythagorean theorem. The velocity of each reflective content of product 16 can be calculated by dividing the displacement of the center of each reflective image 52 by the amount of time that elapsed between the first and second analyzed wave images.

Figure 4A:
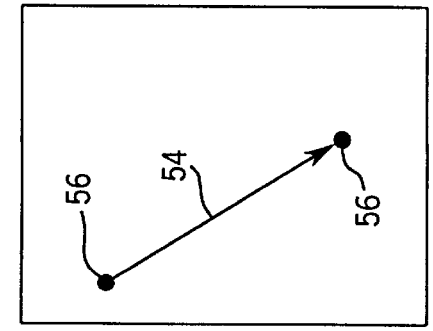
FIG. 4 is a five-part representation of a method for establishing a vector for a reflective content of a flowable product in accordance with the present invention.
Figure 4B:
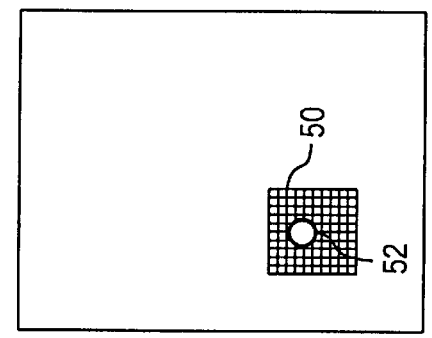
Figure 4C:
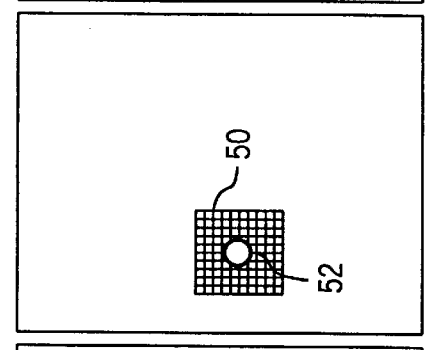
Figure 4D:
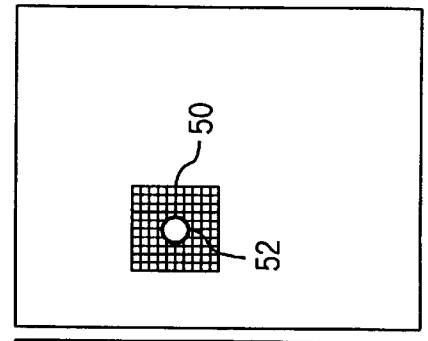
Figure 4E:
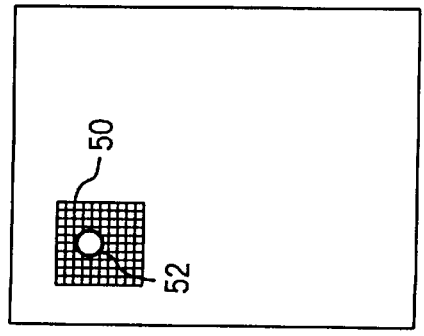

In the preferred embodiment of the present invention, vectors 54 are established by processing unit 10 by analyzing more than two separate wave images, as depicted in FIG. 4E. As depicted in FIG. 4, processing unit 10 analyzes four separate wave images, A, B, C, and D, in order to establish vectors 54. As above-discussed, in the preferred embodiment of the present invention, the mass center x, y coordinates of the reflective contents of the first and last images will be used to calculate the vector 54. In those cases in which more than two wave images are analyzed, the analyzed wave images can be relatively close in time to one another, thereby providing greater assurances that processing unit 10 is tracking single reflective contents and creating vectors 54 for each reflective content. In one embodiment of the present invention, processing unit 10 is configured such that it confirms that a single reflective content is being tracked by confirming that the mass of the reflective content, as determined by the sum of the pixel gray scale values for the image of the reflective content, is substantially constant from frame-to-frame. Nevertheless, vectors 54 can be established using any two or more separate wave images taken at separate times without departing from the scope of the present invention. All intermediate coordinate values are used only for continuous tracking purposes.

Processing unit 10 performs a statistical analysis of vectors 54 for the purpose of calculating a mean displacement or a mean velocity for the reflective contents of product 16. As above-noted, the velocity of each reflective content of product 16 is proportional to the displacement of each reflective content of product 16. Therefore, either the displacement or the velocity of each reflective content of product 16 can be used in performing the statistical analysis. The processing unit 10 then compares the calculated mean displacement or mean velocity to an acceptable range of displacements or velocities for reflective contents of product 16. In addition, processing unit 10 determines a statistical skewness for the displacements or velocities of the reflective contents of product 16. The resulting skewness also is compared to an acceptable range of skewness for the displacements or velocities of reflective contents of product 16. In the event that the mean displacement, the mean velocity, or the skewness is not within the acceptable range, processing unit 10 generates an error signal indicating that product 16 is not acceptable. In the embodiment of the present invention depicted in FIG. 3, processing unit 10 activates piston rejection mechanism 14 when processing unit 10 generates an error signal for the purpose of discarding the container 17 that contains the unacceptable product 16.

It will be appreciated that other statistical analyses can be conducted using dynamic testing techniques. For example, processing unit 10 can be configured such that it analyzes the coordinates of each vector for the purpose of determining whether the reflective contents of product 16 are moving at substantially the same rate in all areas of the reflected image. In the event that reflective contents in certain areas of the reflected image are moving at rates substantially different than the remainder of product 16, or in the event that reflective contents in certain areas of the reflected wave image are moving in substantially different directions than the remainder of product 16, it is likely that product 16 is undergoing localized changes, e.g., localized spoilage or localized coagulation. Processing unit preferably generates an error signal in the event that the flow rates or directions of reflective contents in a certain area of the reflected wave image are substantially different than the flow rates or directions of reflective contents in the remainder of the reflected image. In addition, processing unit 10 can be configured such that it analyzes the head and tail coordinates for each vector for the purpose of determining whether they are evenly distributed through the reflected wave image. In the event that product 16 is undergoing localized changes in characteristics, e.g., viscosity, there may be certain areas of the reflected wave image through which no vector passes. If processing unit 10 detects an inconsistency in the distribution of coordinates of the established vectors, it generates an error signal.

Acceptable ranges for mean displacement, mean velocity, and skewness are calculated on a product-by-product basis due to variations in product viscosity and particulate content. In addition, acceptable ranges for these parameters must be determined based upon the speed at which product 16 is agitated and the length of time that is allowed to lapse between the agitation of product 16 and the ultrasonic testing of product 16. For this reason, acceptable ranges are preferably established by conducting dynamic testing in the above-discussed manner on products 16 that have been determined to be acceptable using known testing methods such as chemical and visual testing. The acceptable ranges for these parameters are preferably established using the same rate of agitation and the same time delay between agitation and ultrasonic testing that will be used in the actual testing procedure.

The above-discussed dynamic testing and analysis techniques can be used for the purpose of analyzing a flowing liquid. For example, the above-referenced techniques can be used to analyze blood flowing through a blood vessel, including blood that has a contrast or imaging agent added thereto. Other fluids flowing through conduits or pipelines also can be objectively analyzed using the techniques of the present invention. By establishing vectors for reflective contents of the flowing liquid, it is possible to identify areas in which the liquid is encountering certain flow parameters. For example, a dynamic test conducted as above-described can be used to detect areas in which the flowable liquid encounters counterflow, low-flow, or no-flow situations. In this application of the instant invention, processing unit 10 is configured to establish vectors representing the movement of reflective contents of the flowable liquid/product 16 as above-discussed. Processing unit 10 also compares the resulting vectors to an acceptable range of vector statistical parameters as above-discussed for the purpose of determining whether the flowable liquid/product 16 is flowing in an acceptable fashion or if there is a flow condition that requires correction. As above-discussed, processing unit 10 preferably is configured to generate an error signal when an unacceptable flow condition is detected.

Although the apparatus and method of the present invention have been described in detail herein with respect to certain preferred embodiments, it will be apparent to one of ordinary skill in the art that various modifications to the present invention without departing from the intended spirit and scope of the invention as claimed in the appended claims.

What is claimed is:

1. A method for ultrasonically analyzing a flowable liquid for acceptability, said method comprising:

providing a flowable liquid to be quality tested;

providing means for generating and receiving ultrasonic waves;

providing a processing unit;

providing an agitator to agitate said flowable liquid;

agitating said flowable liquid using said agitator;

placing said means for generating and receiving ultrasonic waves in ultrasonic contact with said flowable liquid;

directing a plurality of ultrasonic waves into said flowable liquid using said means for generating and receiving ultrasonic waves;

receiving a plurality of ultrasonic waves from said flowable liquid using said means for generating and receiving ultrasonic waves;

converting said plurality of received ultrasonic waves into a plurality of respective wave image signals using said means for generating and receiving ultrasonic waves;

transmitting said plurality of wave image signals from said means for generating and receiving ultrasonic waves to said processing unit;

processing said plurality of wave image signals using said processing unit, said processing step including the steps of:

establishing respective vectors for a plurality of ultrasonically reflective contents of said flowable liquid; and statistically comparing said respective vectors for said plurality of ultrasonically reflective contents to a predetermined, qualitatively acceptable range of vectors.

2. A method for ultrasonically analyzing a flowable liquid for acceptability in accordance with claim 1, wherein said step of statistically comparing includes calculating a mean velocity of said respective vectors for said plurality of ultrasonically reflective contents of said flowable liquid and comparing said mean velocity to a predetermined, qualitatively acceptable range of mean velocities.

3. A method for ultrasonically analyzing a flowable liquid for acceptability in accordance with claim 2, wherein said step of statistically comparing further includes calculating a skewness of said respective vectors for said plurality of ultrasonically reflective contents of said flowable liquid and comparing said skewness to a predetermined, qualitatively acceptable range of skewness.

4. A method for ultrasonically analyzing a flowable liquid for acceptability in accordance with claim 1, wherein said step of statistically comparing includes identifying a head coordinate and a tail coordinate for each of said respective vectors and comparing said head and tail coordinates to a predetermined, qualitatively acceptable range of coordinates.

5. A method for ultrasonically analyzing a flowable liquid for acceptability in accordance with claim 1, wherein said step of statistically comparing includes establishing a direction for each of said respective vectors and comparing said directions to a predetermined, qualitatively acceptable range of directions.

6. A method for ultrasonically analyzing a flowable liquid for acceptability in accordance with claim 1, wherein said step of establishing respective vectors includes:
   analyzing a first of said plurality of wave image signals to identify respective first positions of said plurality of ultrasonically reflective contents of said flowable liquid;
   analyzing a second of said plurality of wave image signals to identify respective second positions of said plurality of ultrasonically reflective contents of said flowable liquid; and
   creating a vector for each of said plurality of reflective contents of said flowable liquid using said first and second positions of said plurality of reflective contents of said flowable liquid.

7. A method for ultrasonically analyzing a flowable liquid for acceptability in accordance with claim 1, wherein said step of comparing respective vectors includes calculating a mean magnitude of said respective vectors for said plurality of ultrasonically reflective contents of said flowable liquid and comparing said mean magnitude to a predetermined, qualitatively acceptable range of mean magnitudes for said vectors.

8. A system for ultrasonically analyzing a flowable liquid for acceptability, said system comprising:
   a conveyor to convey a flowable liquid, said conveyor including an agitator to agitate a flowable liquid along said conveyor;
   means for generating and receiving ultrasonic waves, said means for generating and receiving ultrasonic waves constructed to convert a received ultrasonic wave into a wave image signal;
   means for selectively placing said means for generating and receiving ultrasonic waves in ultrasonic contact with a unit of a flowable liquid along said conveyor;
   a processing unit to analyze a plurality of wave image signals generated by said means for generating and receiving ultrasonic waves, said processing unit coupled to said means for generating and receiving ultrasonic waves, said processing unit including:
      means for establishing respective vectors for a plurality of reflective contents of said flowable liquid; and
      means for statistically comparing said respective vectors of said plurality of reflective contents to a predetermined, qualitatively acceptable range of vectors; and
   means for removing units of flowable liquid determined to be outside of the qualitatively acceptable range of vectors.

9. A system for ultrasonically analyzing a flowable liquid for acceptability in accordance with claim 8, wherein said agitator includes a rotatable platform and a selectively operational drive to rotate said rotatable platform.

10. A method for ultrasonically analyzing a flowing liquid for acceptability, said method comprising:
    providing a flowing liquid to be ultrasonically analyzed;
    providing means for generating and receiving ultrasonic waves, said means for generating and receiving ultrasonic waves constructed to convert a received ultrasonic wave into a wave image signal;
    providing a processing unit;
    placing said means for generating and receiving ultrasonic waves in ultrasonic contact with said flowing liquid;
    directing a plurality of ultrasonic waves into said flowing liquid using said means for generating and receiving ultrasonic waves;
    receiving a plurality of ultrasonic waves from said flowing liquid using said means for generating and receiving ultrasonic waves and converting said plurality of received ultrasonic waves into a plurality of wave image signals;
    transmitting said plurality of wave image signals from said means for generating and receiving ultrasonic waves to said processing unit;
    processing said plurality of wave image signals using said processing unit, said processing step including the steps of:
       establishing respective vectors for a plurality of ultrasonically reflective contents of said flowing liquid; and
       statistically comparing said respective vectors for said plurality of ultrasonically reflective contents to a predetermined, qualitatively acceptable statistical range of vectors.

11. A method for ultrasonically analyzing a flowing liquid for acceptability in accordance with claim 10, wherein said step of statistically comparing includes calculating a mean velocity of said respective vectors for said plurality of ultrasonically reflective contents of said flowing liquid and comparing said mean velocity to a predetermined, qualitatively acceptable range of mean velocities.

12. A method for ultrasonically analyzing a flowing liquid for acceptability in accordance with claim 10, wherein said step of statistically comparing further includes calculating a skewness of said respective vectors for said plurality of ultrasonically reflective contents of said flowing liquid and comparing said skewness to a predetermined, qualitatively acceptable range of skewness.

13. A method for ultrasonically analyzing a flowing liquid for acceptability in accordance with claim 10, wherein said step of establishing respective vectors includes:
    analyzing a first of said plurality of wave image signals to identify respective first positions of said plurality of ultrasonically reflective contents of said flowing liquid;
    analyzing a second of said plurality of wave image signals to identify respective second positions of said plurality of ultrasonically reflective contents of said flowing liquid; and
    creating a vector for each of said plurality of reflective contents of said flowing liquid using said first and second positions of said plurality of reflective contents of said flowing liquid.

14. A method for ultrasonically analyzing a flowing liquid for acceptability in accordance with claim 10, wherein said step of statistically comparing includes identifying a head coordinate and a tail coordinate for each of said respective vectors and comparing said head and tail coordinates to a predetermined, qualitatively acceptable range of coordinates.

15. A method for ultrasonically analyzing a flowing liquid for acceptability in accordance with claim 10, wherein said step of statistically comparing includes establishing a direction for each of said respective vectors and comparing said directions to a predetermined, qualitatively acceptable range of directions.

16. A method for detecting spoilage in a flowable product, said method comprising the steps of:

provinding a flowable product;

providing means for generating and receiving ultrasonic waves, said means for generating and receiving ultrasonic waves constructed to convert a received ultrasonic wave into a wave image signal;

providing a processing unit;

providing an agitator to agitate said flowable product;

agitating said flowable product using said agitator;

placing said means for generating and receiving ultrasonic waves in ultrasonic contact with said flowable product;

directing a plurality of ultrasonic waves into said flowable product using said means for generating and receiving ultrasonic signals;

receiving a plurality of ultrasonic waves from said flowable product using said means for generating and receiving ultrasonic signals;

converting said plurality of received ultrasonic waves into a plurality of wave image signals;

transmitting said plurality of wave image signals from said means for generating and receiving ultrasonic signals to said processing unit; and processing said plurality of wave image signals using said processing unit, said processing step including the steps of:

establishing respective vectors for a plurality of ultrasonically reflective contents of said flowable product;

statistically comparing said respective vectors for said plurality of ultrasonically reflective contents to a predetermined, qualitatively acceptable range of vectors; and generating a signal indicating whether said respective vectors are within said predetermined, qualitatively acceptable range of vectors.

17. A method for detecting spoilage in a flowable product in accordance with claim 16, wherein said step of establishing respective vectors includes:

analyzing a first of said plurality of wave image signals on a pixel basis and calculating a gray scale value for each pixel;

identifying pixels having a gray scale value at least equal to a threshold gray scale value, thereby identifying a plurality of ultrasonically reflective components in said flowable product;

identifying a first center position for each of said plurality of ultrasonically reflective components in said flowable product;

analyzing a second of said plurality of wave image signals on a pixel basis and calculating a gray scale value for each pixel;

identifying pixels having a gray scale value at least equal to a threshold gray scale value, thereby identifying a plurality of ultrasonically reflective components in said flowable product;

identifying a second center position for each of said plurality of ultrasonically reflective components in said flowable product; and establishing a vector for each of said plurality of ultrasonically reflective components in said flowable product, each said vector having a tail at said first center position and a head at said second center position.

* * * * *